United States Patent [19]
Gu

[11] Patent Number: 5,854,682
[45] Date of Patent: Dec. 29, 1998

[54] METHOD AND APPARATUS FOR SURFACE PRESSURE MAPPING OF ROTATING OBJECTS BY SYNCHRONIZED OPTICAL IMAGING OF LUMINESCENT COATING

[76] Inventor: Xijia Gu, 113 Marbury Crescent, North York, Ontario, Canada, M3A 2G3

[21] Appl. No.: 848,756

[22] Filed: May 1, 1997

[51] Int. Cl.⁶ .......................... G01N 21/84; G01M 9/00; G01L 9/00
[52] U.S. Cl. ................. 356/426; 73/147; 73/705
[58] Field of Search .............................. 356/426; 73/147, 73/705

[56] References Cited

U.S. PATENT DOCUMENTS

| | | | |
|---|---|---|---|
| 5,307,675 | 5/1994 | Mosharov et al. | 73/147 |
| 5,359,887 | 11/1994 | Schwab et al. | 73/147 |
| 5,446,334 | 8/1995 | Gaffney | 250/338.3 |
| 5,612,492 | 3/1997 | Schwab et al. | 73/147 |

OTHER PUBLICATIONS

An Optical Pressure Measurement System for Wind Tunnel Testing, X.J. Gu, J. Coll, D. Lye, F.A. Ellis, V.D. Nguyen, J. Bureau, Applications of *Photonic Technology*, Edited by G.A. Lampropoulos et al., Plemum Press, New York, 1995, pp. 271–274.

Luminescent Barometry in Wind Tunnels, Janet Kavandi, James Callis, Martin Gouterman, Gamal Khalil, Daniel Wright and Edmond Green, *Department of Chemistry, BG–10, University of Washington, Seattle, Washington* 91895; David Burns, *Center for Bioengineering, WD–12, University of Washington, Seattle, Washington,* 98195; and Blair McLachlan, *NASA–Ames Research Center, Moffett Field, California 94035* (Received 27 Dec. 1989, accepted for publication 28 Mar. 1990) pp. 3340–3347.

Advanced Materials, Phosphorescent Oxygen sensors Utilizing Sulfur–Nitrogen–Phosphorus Polymer Matrices, VCH Verlagsgesellschaft mbH D–69469 Weinheim, 1996 *Adv. Mater* 1996, 8, No. 9, pp. 768–771.

*Primary Examiner*—Frank G. Font
*Assistant Examiner*—Jason D. Vierra-Eisenberg
*Attorney, Agent, or Firm*—Lynn C. Schumacher; Hill & Schumacher Dowell & Dowell, P.C.

[57] ABSTRACT

The present invention provides a new synchronized optical method for measuring surface pressure on rotating objects such as propellers or other rotating objects. The technique is based on the phenomenon of oxygen quenching of luminescence coatings and synchronized optical imaging. A surface coating, referred to as a pressure sensitive paint (PSP), is formed by mixing photo-luminescence molecules in an oxygen permeable polymer. The luminescence excited by an appropriate light source decreases as the oxygen concentration rises due to quenching. As a result, the luminescence intensity of light emitted from the coating varies as a function of the partial pressure of oxygen. A digital camera measures the luminescence intensity distribution over the object and the pressure distribution can be computed.

10 Claims, 5 Drawing Sheets

METHOD AND APPARATUS FOR SURFACE PRESSURE MAPPING OF ROTATING OBJECTS BY SYNCHRONIZED OPTICAL IMAGING OF LUMINESCENT COATING

FIELD OF THE INVENTION

The present invention relates to a method and device for pressure mapping of rotating objects by synchronized optical imaging of luminescent paint.

BACKGROUND OF THE INVENTION

Aerodynamic data of aircraft propellers and other rotating objects are important for optimization of blade and spinner geometries for maximum aerodynamic efficiency and for providing aerodynamic loading information. To generate aerodynamic data, several methods have been used. The one was strip analysis technique which involves the calculation of the aerodynamic angle of attack at each radius along a lifting line from a solution of the equations describing the distribution of circulation in the wake, see for example Wong P. C. W., Maina M. Forsey C. R., Bocci A. J. "SINGLE AND CONTRA-ROTATION HIGH SPEED PROPELLERS: FLOW CALCULATION AND PERFORMANCE PREDICTION:, ICAS 88-2.4.2.1988; and Bocci, A. J. and Morrison J. I., "A REVIEW OF ARA RESEARCH INTO PROPELLER AERODYNAMIC PREDICTION METHODS", AGARD-CP-366, 1984. The other was the scaled-model test employing pressure tapped blades and spinner to obtain a database for high speed propellers as disclosed in N. Scrase and M. Maina, International Council of Aeronautical Science, ICAS-94-6.1.2.

Luminescent barometry on stationary airfoils in wind tunnels has been previously reported, see for example Janet Kavandi, James Callis, Martin Gouterman, Gamal Khalil, Daniel Wright, Edmond Green, David Burns and Blair McLachlan, LUMINESCENT BAROMETRY IN WIND TUNNELS, Rev. Sci. Instrum., Vol. 61, No. 11, November 1990 and X. J. Gu, J. Coll, D. Lye, F. A. Ellis, V. D. Nguyen and J. Bureau, AN OPTICAL PRESSURE MEASUREMENT SYSTEM FOR WIND TUNNEL TESTING, in Applications of Photonic Technology, Ed. G. A. Lampropouleos et al., Plenum Press, New York, 1995, which is incorporated herein by reference.

It is very difficult to obtain pressure distribution information on rotating objects such as propellers or water turbines. It would be very advantageous to be able to obtain this type of data in real time use of a rotating object. The use of pressure taps is problematic since it involves perturbing the surface of the propeller. Placing pressure taps on rotating objects is problematic due to attachments added to the pressure taps which make rotation of the object inconsistent. Therefore, it would be very advantageous to provide a remote sensing method for detecting the surface pressure on the surface of a rotating object.

SUMMARY OF THE INVENTION

A new optical method is disclosed for measuring surface pressure on rotating objects. The technique is based on the phenomenon of oxygen quenching of luminescence and synchronized optical imaging. A surface coating, referred to as a pressure sensitive paint (PSP), is formed by mixing photo-luminescence molecules in an oxygen permeable polymer. The luminescence excited by an appropriate light source decreases as the oxygen concentration rises due to quenching. As a result, the luminescence intensity of light emitted from the coating varies as a function of the partial pressure of oxygen. A digital camera measures the luminescence intensity distribution over the model and the pressure distribution can be computed. This method, referred to as an optical pressure measurement system (OPMS) has been tested in small high speed wind tunnels.

The present invention provides a method of surface pressure mapping rotating objects comprising providing an object having an outer surface and applying to the outer surface a pressure sensitive photoluminescent paint coating. The method includes rotating the object at a preselected rotational velocity and directing a train of light pulses from a light source at the rotating object. The light pulses are synchronized to the rotational velocity of the rotating object and the light pulses are of a first wavelength. The method includes detecting and storing photoluminescent light intensity due to emission from the photoluminescent pressure sensitive paint on the rotating object of the light pulses impinging on the coated rotating object. The method includes processing the photoluminescent light intensity to convert the photoluminescent light intensity into a pressure distribution over the surface of the rotating object.

In another aspect, the present invention provides a method of surface pressure mapping rotating objects. The method comprises providing an object having an outer surface and applying to the outer surface a pressure sensitive photoluminescent paint coating. The object is then rotated at a preselected rotational velocity and directing a train of light pulses from a light source at the rotating object with the light pulses being synchronized to the rotational velocity of the rotating object with the light pulses being of a first wavelength. The method includes filtering photoluminescent light emitted from the photoluminescent pressure sensitive paint on the rotating object to filter out light of the first wavelength, and detecting and storing the filtered photoluminescent light and converting the filtered photoluminescent light into a first image. The method includes providing a second photoluminescent image of the object measured when the object is stationary and ratioing the second image of the stationary object to the image of the rotating object, and converting the ratio into a pressure distribution over the surface of the rotating object.

The present invention provides a system for measurement of surface pressure on an object being rotated. The system comprises a photoluminescent pressure sensitive paint which can be coated onto a surface of the object to be rotated. Included is a light source for emitting a train of light pulses directed at the object, the light source including means for synchronizing the light source to the rotational velocity of the object, the light source emitting light at a first wavelength. The system includes a photodetection means for detecting photoluminescent light intensity emitted from the photoluminescent pressure sensitive paint and processing means for storing and processing the emitted photoluminescent light intensity to convert such intensity into a pressure distribution over the surface of the rotating object.

BRIEF DESCRIPTION OF THE DRAWINGS

The following is a description, by way of example only, of a method and device for optical surface pressure mapping of rotating objects in accordance with the present invention, reference being had to the accompanying drawings, in which.

DETAILED DESCRIPTION OF THE INVENTION

Figure 1:
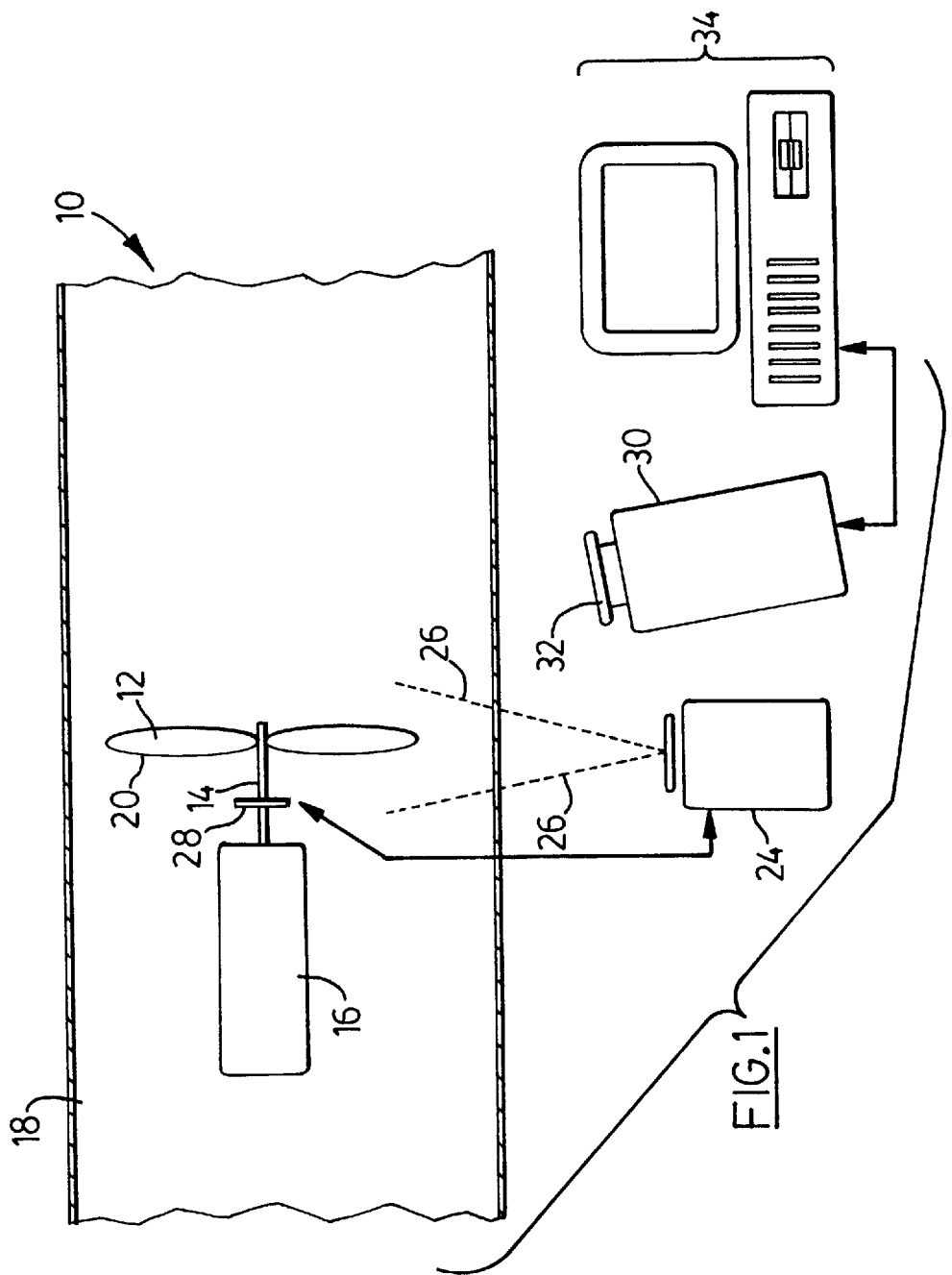
FIG. 1 is a schematic diagram of a system and apparatus for the optical surface pressure mapping of a propeller surface/by synchronized optical imaging of luminescent paint according to the present invention.

With reference to FIG. 1, a schematic diagram of the system and apparatus for making optical surface pressure measurements, or optical pressure measurement system (OPMS) is shown generally at 10. A propeller 12 is mounted on the end of a propeller shaft 14 connected to a motor 16 for rotation about the longitudinal axis of shaft 14. The propeller 12 and motor 16 are located in a 6×8 feet wind tunnel 18. The surface of propeller 12 is coated with a thin surface coating 20 of a pressure sensitive paint (PSP), which is formed by mixing photo-luminescence molecules in an oxygen permeable polymer. The luminescence excited by an appropriate light source decreases as the oxygen concentration rises due to quenching. As a result, the luminescence intensity of light emitted from the coating varies as a function of the partial pressure of oxygen, see for example Zhen Pang, Xijia Gu, Ahmad Yekta, Zahra Masoumi, John B. Coll, Mitchell A. Winnik and Ian Manners, PHOSPHORESCENT OXYGEN SENSORS UTILIZING SULFUR-NITROGEN-PHOSPHORUS POLYMER MATRICES; Adv. Mater. 1996, 8, No.9, which is incorporated herein by reference.

A strobe light source 24 emits a train of light pulses 26 which are synchronized to the rotation of propeller 12 by a sensor 28 coupled to propeller shaft 14. A detector such as a charge coupled device (CCD) digital camera 30 records the luminescence image over the model and the pressure distribution can be computed. A band pass filter 32 is positioned in front of the camera aperture so that CCD camera 30 only detects the luminescence from the propeller surface which is inversely proportional to the pressure. The output of CCD camera 30 is input into processor 34.

The pulse width of the flash lamp 24 is set to between about 1 to about 2 microseconds so that the CCD camera only sees the propeller 12 in a fixed or frozen position. At a propeller speed of 4000 RPM and with a blade length of 1 foot (scaled model), the blade image on the CCD camera would be blurred to be less than one pixel.

Image analysis was used to convert the luminescent light distribution into the pressure distribution. To correctly calculate the pressure distribution over the propeller blade, two images are acquired. One image was taken when the propeller was rotating and tunnel wind on (called "on-image") where the pressure distribution on the blade surface was unknown. The other image was taken when the propeller 12 and tunnel wind were stopped (called "off-image"), in that case, the pressure distribution was a constant over the blade surface. The off-image was divided by the on-image and the resulting image has the darker color corresponding to lower pressure and the lighter color corresponds to higher pressure, as shown in FIG. 2.

The strobe light source 24 used was a Xenon lamp (Model MVS-220, EG & G Electro-Optics) with a mean flash power of 40 Watts. The detector 30 used was a liquid nitrogen cooled CCD camera (Model LN/CCD, Princeton Instruments Inc.) with 578×384 pixels in a cell size of 13.25×8.83 mm$^2$. The camera 30 has a low dark noise of 0.05 counts/(pixel@second)$^{0.5}$ and high dynamic range of 14 bits which are necessary for this test. The luminescent light from the outer surface of propeller 12 was collected with a zoom lens (Nikon, 28–85 mm, 1:3.5–4.5) and imaged onto the CCD camera 30.

A calibration curve was measured by taking the luminescence intensity readings over a pressure range of 0.05 to 2.5 atm. The resulting intensity reading at ambient pressure, 1.0 atm was taken as $I_o$. A nearly linear relationship between $I_o/I$ versus $p/p_o$ was obtained, as predicted by the Stern-Volmer relation. The intercept and the slope were determined by least-squares fitting as 0.52±0.02 and 0.44±0.04 respectively. The sum of these two numbers is unity within experimental error.

Figure 2:
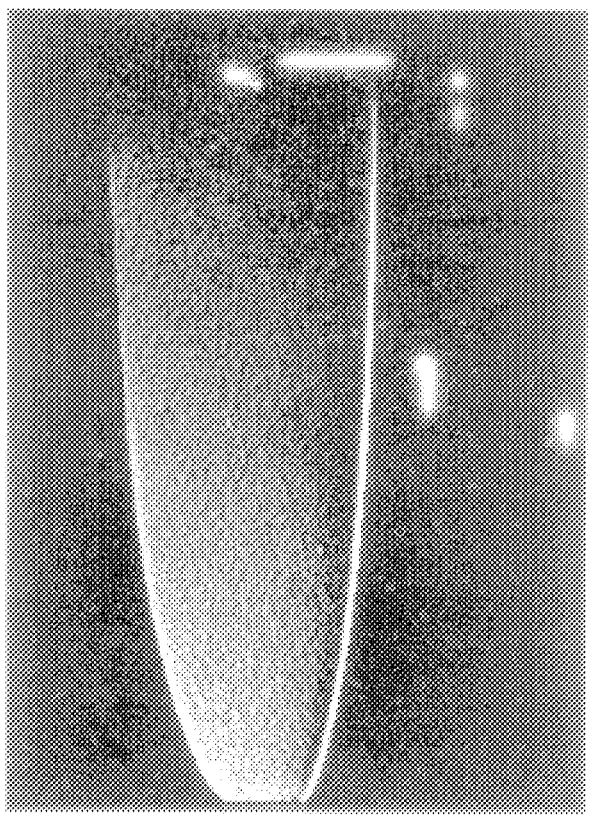
FIG. 2 illustrates the intensity ratioed image of a propeller blade rotating at 4150 RPM with a wind speed of 300 feet/second in a 6×8 feet wind tunnel.

FIG. 2 shows a processed image for the suction side of the propeller blade 12 rotating at 4150 RPM, at a blade angle of 52° and with a wind speed of 300 feet/sec. The direction of rotation of the propeller is count-clock-wise. The pixel intensity in this image is proportional to pressure. It can be seen that there is a high pressure build up at the leading edge, followed by a lower pressure region, the pressure increases towards the trailing edge.

Figure 3A:
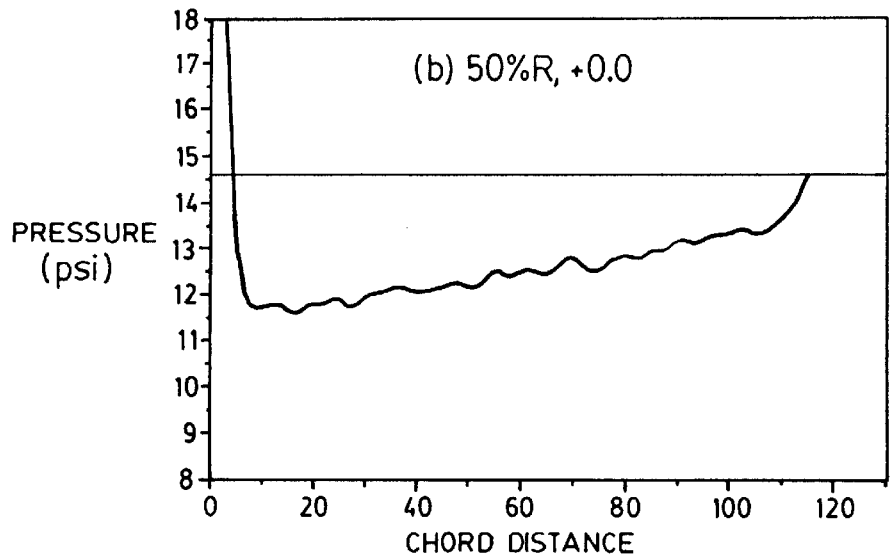
FIG. 3a shows optical surface pressure mapping measurements/of pressure distributions at 50% of full radius at 6600 RPM, blade angle of 32° and a wind speed of 200 feet/second in a 6×8 feet wind tunnel.
Figure 3B:
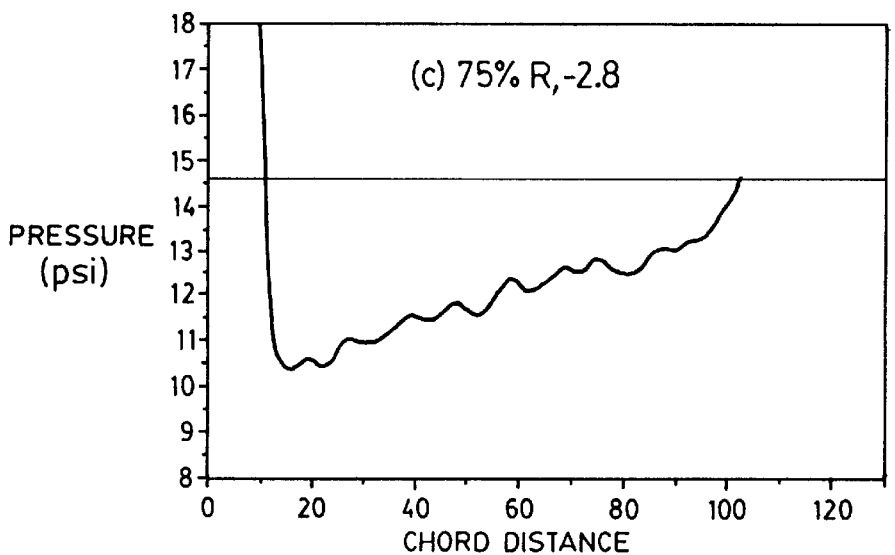
FIG. 3b shows optical surface pressure mapping measurements of pressure distributions at 75% full radius at 6600 RPM, blade angle of 32° and a wind speed of 200 feet/second in a 6×8 feet wind tunnel.
Figure 3C:
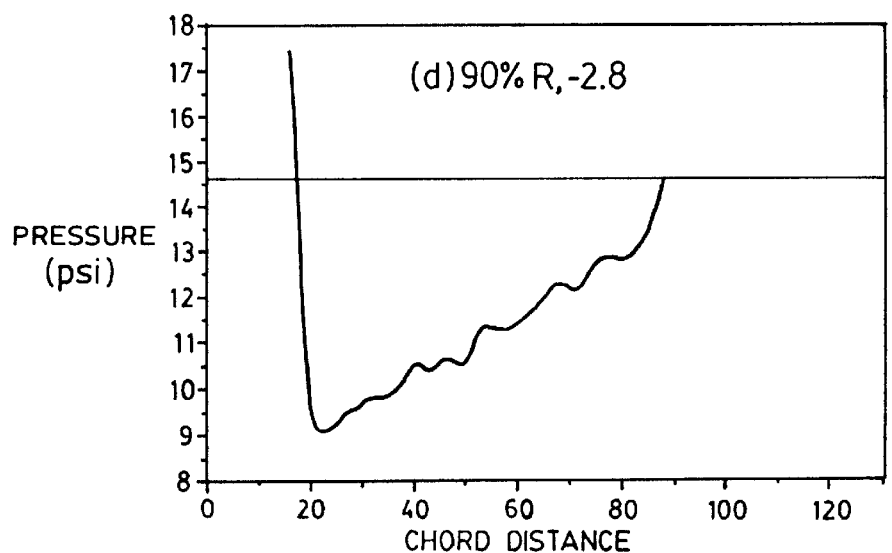
FIG. 3c shows optical surface pressure mapping measurements of pressure distributions at 90% full radius at 6600 RPM, blade angle of 32° and a wind speed of 200 feet/second in a 6×8 feet wind tunnel.

FIGS. 3a–c show the pressure data for propeller 12 rotating at 6600 RPM and wind speed of 200 ft/sec which simulates take-off conditions. The intensity ratio $I_o/I$ was measured at the cross sections taken at various radial positions on the blade, such as at 50%, 75% and 90% of full radius respectively. The pressure distributions across these sections were calculated using the calibration curve and were plotted in FIGS. 3a, 3b, and 3c. The intensity ratio $I_o/I$ was scaled down by a factor of 1.03 (to correct the different illumination intensities for the on and off-images) so the pressure at the tail edge at 50% of radius can match the atmospheric pressure. These results clearly show that pressure distributions can be measured over the coated surface of a rotating object.

The pressure distributions in FIGS. 3a to 3c show two key features: 1) there is a sharp pressure increase at the leading edge followed by a pressure "well"; the pressure then increases towards the trailing edge; and 2) the pressure "well" becomes deeper at large radial distance (~11.7 psi at 50%R, ~10.5 psi at 75%R and ~9.0 psi at 90%R respectively).

The plots shown in FIGS. 3b and 3c are down shifted by 2.8 and 5.6 psi respectively so the pressures at their tail edges match the atmospheric pressure.

Figure 4A:
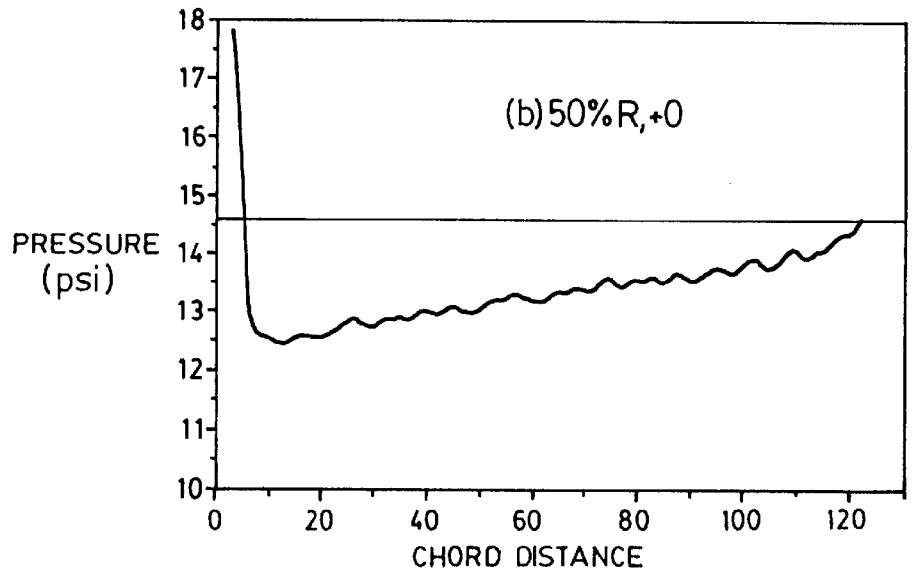
FIG. 4a shows the optical surface pressure mapping measurements of pressure distributions at 50% full radius at 4150 RPM, blade angle of 52° and a wind speed of 300 feet/second in a 6×8 feet wind tunnel.
Figure 4B:
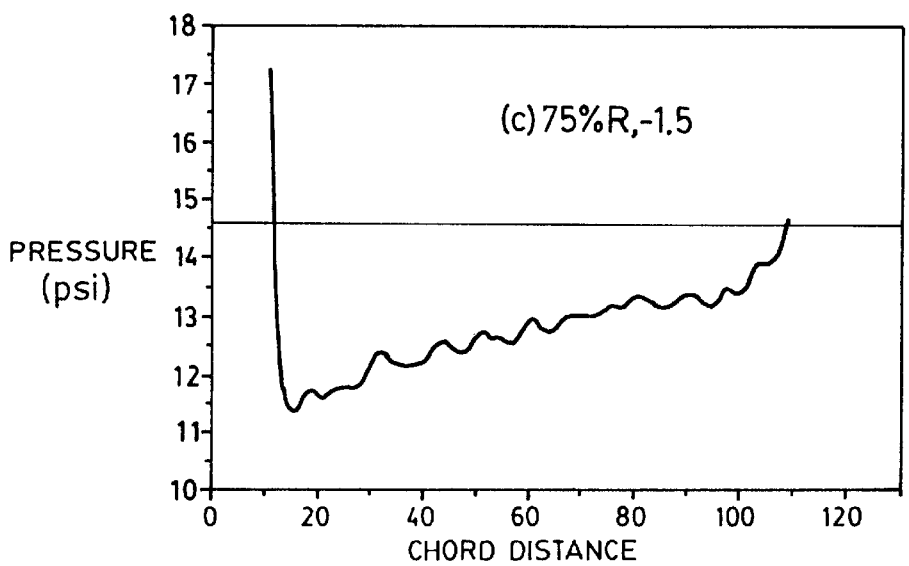
FIG. 4b shows the optical surface pressure mapping measurements of pressure distributions at 75% full radius at 4150 RPM, blade angle of 52° and a wind speed of 300 feet/second in a 6×8 feet wind tunnel.
Figure 4C:
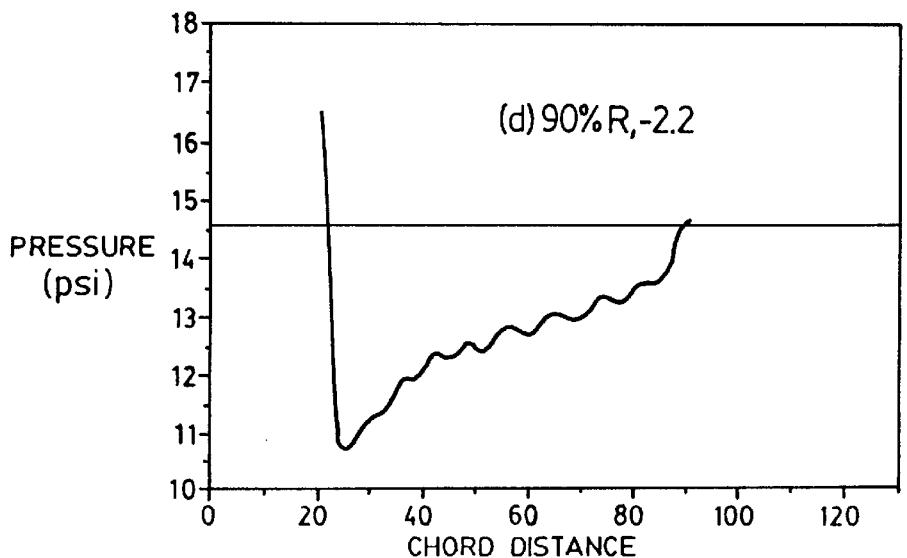
FIG. 4c shows the optical surface pressure mapping measurements of pressure distributions at 90% full radius at 4150 RPM, blade angle of 52° and a wind speed of 300 feet/second in a 6×8 feet wind tunnel.

Similar measurements were carried out at a speed of 4150 RPM and wind speed of 300 ft/sec that simulates climb-up conditions. The pressure data is shown in FIGS. 4a, 4b and 4c. The pressure distributions show a similar trend as that seen in FIGS. 3a to 3c, except that the pressure "wells" are not as deep due to the lower propeller speed.

Figure 5A:
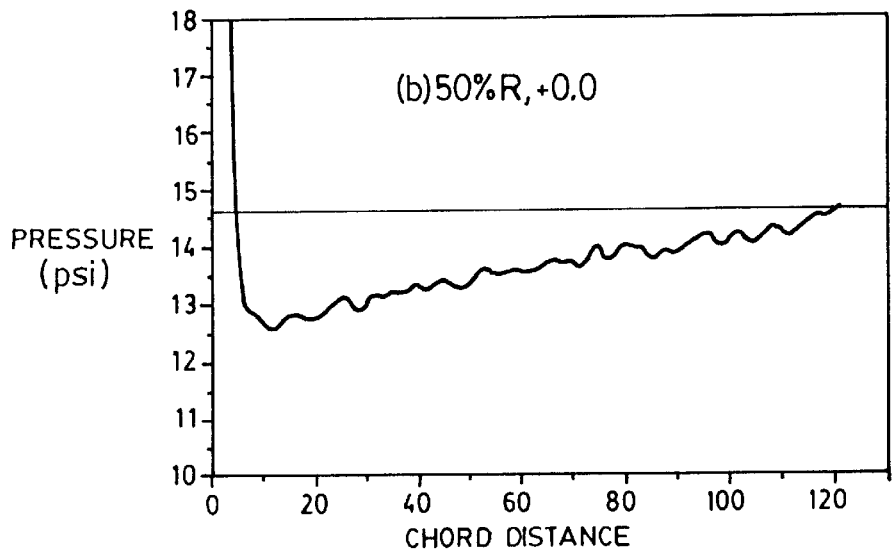
FIG. 5a shows the optical surface pressure measurements of pressure distributions at 50% full radius at 3300 RPM, blade angle of 60° and a wind speed of 355 feet/second in a 6×8 feet wind tunnel.
Figure 5B:
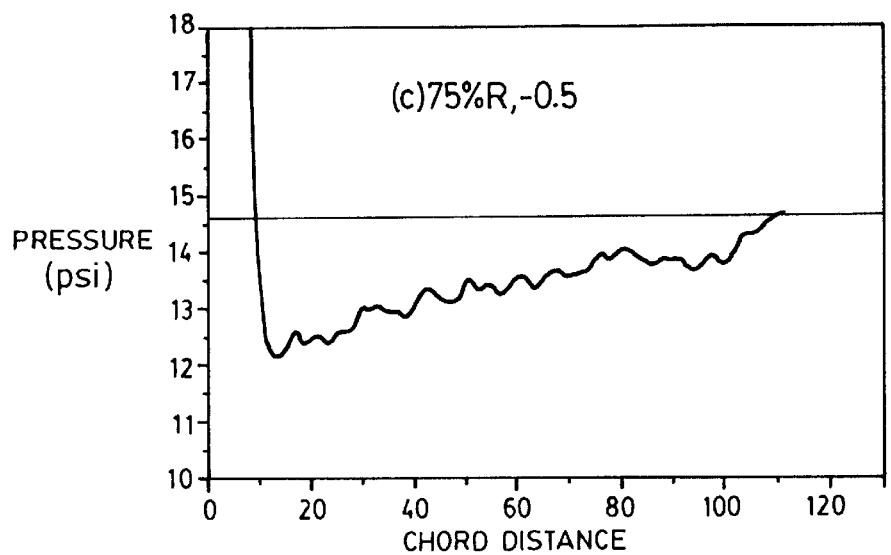
FIG. 5b shows the optical surface pressure measurements of pressure distributions at 75% full radius at 3300 RPM, blade angle of 60° and a wind speed of 355 feet/second in a 6×8 feet wind tunnel.
Figure 5C:
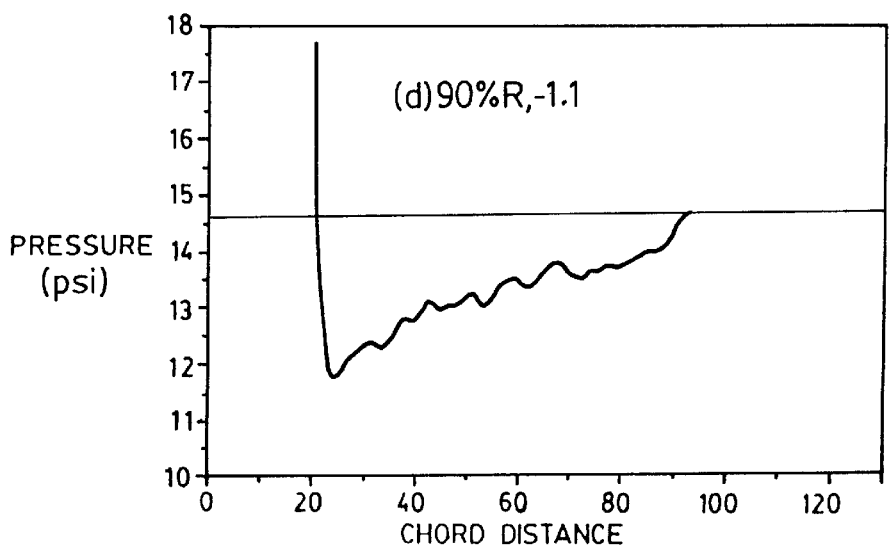
FIG. 5c shows the optical surface pressure measurements of pressure distributions at 90% full radius at 3300 RPM, blade angle of 60° and a wind speed of 355 feet/second in a 6×8 feet wind tunnel.

The pressure data for measurements at 3300 RPM and wind speed of 355 ft/sec that simulates cruise conditions are shown in FIG. 5a, 5b and 5c.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A method of surface pressure mapping rotating objects, comprising;
   a) providing an object having an outer surface and applying to said outer surface a pressure sensitive photoluminescent coating;
   b) rotating said object at a preselected rotational velocity and directing a train of light pulses from a light source at said rotating object, synchronizing said light pulses to said rotational velocity of said object, with said light pulses being of a first wavelength;
   c) detecting and storing a photoluminescent light intensity due to emission from said pressure sensitive photoluminescent coating on said rotating object due to said light pulses impinging on the coated outer surface of the rotating object; and
   d) processing said photoluminescent light intensity to convert said photoluminescent light intensity into an image of a pressure distribution over the surface of the rotating object.

2. The method according to claim 1 wherein the step of detecting said photoluminescent light intensity includes filtering light emitted from said object prior to detection to filter out light of said first wavelength.

3. The method according to claim 2 wherein said light source is a strobe light source and said light pulses have a pulse width in the range of no more than microseconds.

4. The method according to claim 1 including providing a photoluminescent image of said object measured when said object is stationary, and wherein the step of processing said photoluminescent light intensity includes ratioing the image of the object when stationary to said image of the rotating object.

5. A method of surface pressure mapping rotating objects, comprising;
   a) providing an object having an outer surface and applying to said outer surface a pressure sensitive photoluminescent coating;
   b) rotating said object at a preselected rotational velocity and directing a train of light pulses from a light source at the rotating object, said light pulses being synchronized to said rotational velocity of said object, said light pulses being of a first wavelength;
   c) filtering photoluminescent light emitted from said pressure sensitive photoluminescent coating on said rotating object to filter out light of said first wavelength, detecting and storing the filtered photoluminescent light and converting said filtered photoluminescent light into a first image; and
   d) providing a second photoluminescent image of said object measured when said object is stationary and ratioing the second image of the object when stationary to said first image of the rotating object, and converting said ratio into a pressure distribution over the surface of said rotating object.

6. The method according to claim 5 wherein said light source is a strobe light source and said light pulses have a pulse width in no more than microseconds in order to freeze motion of said rotating object.

7. An system for measurement of surface pressure of an object being rotated, comprising;
   a) a photoluminescent pressure sensitive coating material adapted to be coated onto a surface of said object to be rotated;
   b) light source adapted to emitting a train of light pulses directed at said object, said light source including means for synchronizing said light source to rotation of said object, said light source adapted to emitting light at a first wavelength;
   c) photodetection means adapted to detect photoluminescent light intensity emitted from a photoluminescent pressure sensitive material; and
   d) processing means for storing and processing photoluminescent light intensity to convert photoluminescent light intensity into a pressure distribution over a surface of a rotating object.

8. The system according to claim 7 wherein said light source means is a strobe lamp producing light pulses having a pulse width not greater than micro-seconds.

9. The system according to claim 7 wherein said photodetection means includes a charged coupled device camera.

10. The system according to claim 9 wherein said photodetection means includes a band pass filter located in front of said charged coupled device camera to filter out light at said first wavelength.

* * * * *